United States Patent [19]

Sundström

[11] Patent Number: 4,742,828

[45] Date of Patent: May 10, 1988

[54] DISPOSABLE ELECTRODE FOR MONITORING A PATIENT

[75] Inventor: Holger B. Sundström, Göteborg, Sweden

[73] Assignee: Rematra Research, Marketing & Trading Co. S.A., Geneva, Switzerland

[21] Appl. No.: 63,743

[22] Filed: Jun. 16, 1987

Related U.S. Application Data

[63] Continuation of Ser. No. 819,536, Jan. 16, 1986, abandoned.

[30] Foreign Application Priority Data

Jan. 17, 1985 [SE] Sweden .................................. 8500212
Jan. 17, 1985 [SE] Sweden .................................. 8500213

[51] Int. Cl.⁴ .................................................. A61B 5/04
[52] U.S. Cl. .................................... 128/640; 128/641
[58] Field of Search ............................... 128/639–641, 128/644, 798, 802, 803

[56] References Cited

U.S. PATENT DOCUMENTS

| 2,887,112 | 5/1959 | Smith | 128/644 |
| 3,566,860 | 3/1971 | Moe, Jr. | 128/641 |
| 3,606,881 | 9/1971 | Woodson | 128/641 |
| 3,845,757 | 11/1974 | Weyer | 128/641 |
| 3,911,906 | 10/1975 | Reinhold, Jr. | 128/641 |
| 4,237,886 | 12/1980 | Sakurada et al. | 128/798 |

FOREIGN PATENT DOCUMENTS 122258  2/1972  Denmark ........................... 128/641

Primary Examiner—Lee S. Cohen
Attorney, Agent, or Firm—Kane, Dalsimer, Sullivan, Kurucz, Levy, Eisele and Richard

[57] ABSTRACT

A disposable electrode, mainly intended to be fixed on the skin of a patient for noise-free signal detection of body signals and including a carrier element, one side of which is provided with an electric contact and the other side of which carries an adhesive layer and forms the front surface of the carrier element intended to adhere in electrical contact to the skin, wherein the adhesive layer of the front surface of the carrier element has at least one opening in which is fitted a carbon-containing element arranged directly to contact the material of the carrier element.

7 Claims, 1 Drawing Sheet

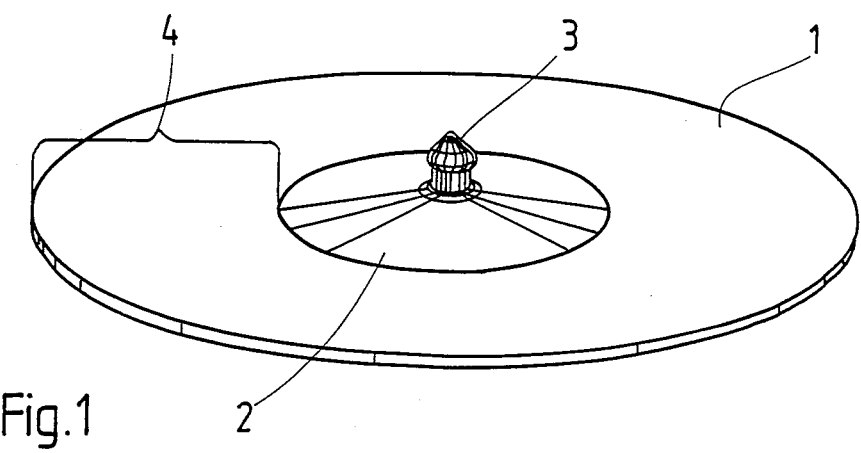
Fig.1
Fig.2
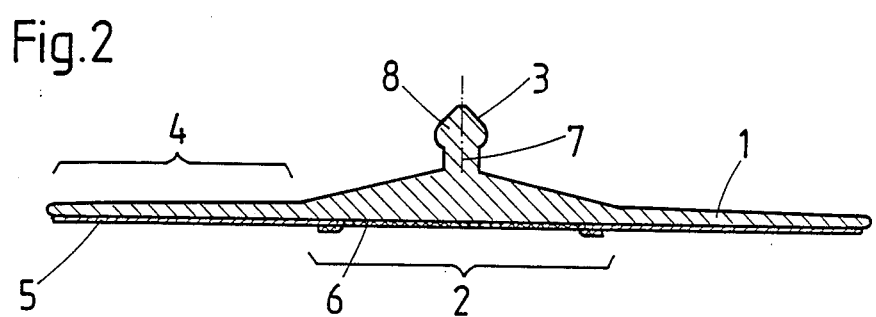
Fig.3
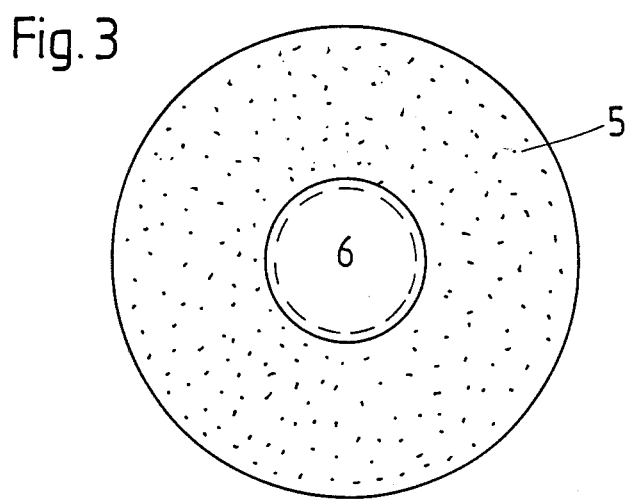

DISPOSABLE ELECTRODE FOR MONITORING A PATIENT

This is a continuation of co-pending application Ser. No. 819,536 filed on 1/16/86, now abandoned.

FIELD OF INVENTION

The present invention refers to a disposable electrode, mainly intended to be fixed on the skin of a patient to achieve noise-free signal detection of signals from the body and including a carrier element, one side of which is provided with an electric contact and the other side of which is provided with an adhesive layer and forms the front surface of the carrier element intended to adhere in electrical contact to the skin.

PRIOR ART

In for example EKG-monitoring there is commonly used both reusable electrodes and disposable electrodes. The disposable electrodes are normally designed with a little plate made by rigid plastic and covered by silver/silver-chloride, which is arranged in the center of a self-adhesive plastic plate and somewhat recessed therein. The silver plate is electrically connected by a cable or contact of metal in order to make possible electrical connection of the electrode to the monitor or oscilloscope. Before the application of the electrode on the skin the recess at the silver plate is filled with an electrically conductirve electrogel. Some types of electrodes on the market are delivered with this electrogel already applied. Silver/silver-chloride is used to achieve low polarization potentials and the gel is used to make the electrode float against the skin, whereby noise in the signal transmission at movements of the patient is avoided. The applying of the gel requires a great carefulness. Too much of the gel will cause the gel to float out over the surface of the electrode which is covered by adhesive. The adherence of the electrode is thereby reduced and the electrode may easily come loose after mounting on the skin of the patient. Too little of the gel gives on the other side bad electrical contact. The elecrtrode types which are already treated with gel is indeed exactly dosed, but have on the other side a limited storing time because the gel will dry out or change its quality by time.

To achieve a noise-free signal detection of the body signals by means of electrodes which are simple to apply it is important that the adhesive capability of the electrodes against the body is very good because noise will otherwise easily appear at movements of the patient owing to the instantaneous changing of impedance. A number of different electrodes intended for this purpose, are available on the market and a possible greater number are disclosed in the patent literature. An electrode device is for instance disclosed in the U.S. Pat. No. 3,911,906 and comprises an adhesive layer applied on a carrier element layer which is electrically conductive by means of carbon powder mixed therein. A metallic contact is arranged in the center of the circular electrode, and more exactly provided by a nailing procedure. The contact consist mainly of a neck which at its top has an enlarged end part and is intended for connection to standardized patient cables. This electrode has a number of disadvantages. Among others the conductive adhesive layer does not give a completely noise-free signal detection from the skin because the impedance is changed at movements in the skin. Because of the fact that the contact must be nailed, the electrode will be expensive to manufacture.

SUMMARY OF THE INVENTION

The main object of the present invention is to provide a disposable electrode of the type mentioned hereabove, which has a simple design and which can be applied radpidly and will give a good electrical contact. A further purpose is that the electrode shall be cheap to manufacture and that it can stand storing during a long period of time. This is achieved according to the invention thereby that the adhesive layer of the front surface of the carrier element has at least one opening wherein is applied a carbon-containing element directly contacting the material of the carrier element.

Another characteristic of the invention is that the carbon-containing element is a plate of woven carbon fibres.

A further characteristic of the invention is that the carrier element and the electrical contact are moulded in one piece from a conductive or semi-conductive material.

BRIEF DESCRIPTION OF THE DRAWINGS

The invention will hereinafter be further described with reference to the enclosed drawings:

FIG. 1 shows an angular top view of a disposable electrode according to the invention, FIG. 2 shows a cut from the side of the disposable electrode and, FIG. 3 is a planar view showing the front surface of the disposable electrode according to the invention.

DESCRIPTION OF THE PREFERRED EMBODIMENTS

FIG. 1 shows a disposable electrode according to the invention in a perspective view from the top. The flat carrier element 1 of the electrode and the electrical contact 3 is made in one piece of a conductive or a semi-conductive material and is moulded preferably from polyethylene admixed with carbon. If carbon is used as conductive material, annoying polarization effects are avoided in the material. The amount of carbon which has to be included depends on the type of carbon used. An appropriate admixture of carbon can be 40–45%.

The carrier element 1 of the electrode is essentially circular and has a broad, thin and flexible bearing collar 4 around its periphery and its center a section 2 is somewhat elevated. The carrier element 1 is designed with an adhesive layer 5 on its underside, which is the contact surface or the front surface, and the adhesive layer is arranged to adhere the electrode to the skin of the patient. In the center of the front surface the adhesive layer has a circular opening having a diameter of for instance 12 mm and being free of adhesive. A contact element, a plate 6, is arranged in the circular area in such a way that the edge of the plate 6 somewhat overlaps and therefore is fixed to the adhesive and thereby is maintained in position. Another way to fix the plate 6 is to melt or burn it against the front surface of the carrier element. The plate 6, which forms the contact surface against the skin of the patient, can preferably consist of a cloth or textile of active carbon fibres with high strength, known e.g. as activated carbon textile manufactured by SIEBE GORMAN, England. The total length of such carbon fibres can be as much as thousands of meters per square centimeter and may essentially facilitate the ion migration between the skin of the patient and the carrier element. The fibre ends of this cloth projects as bruhses from the cloth. These fibre ends will obtain contact with a larger number of carbon particles than e.g. a silver layer, due to the fact that the points of the fibre ends penetrate through the very thin layer covering most charcoal particles. The surface resistance will therefore be reduced very much. the transient resistance will therefore be about ten times lower than that when a pure plastic plate is used.

Alternatively the carbon-containing plate 6 can consist of a glue/gel mixture having an admixture of carbon fibres and/or carbon cyrstals in woven and/or rigid form.

To protect the electrode against undersirable adhering during the storing time it is provided with a protective paper which has a hole in its center (not shown).

To increase the conductive ability to the skin of the patient, the front surface of the electrode is moistened for instance in a basin wherein a wetted-cloth or the like is arranged and contains a physiological sodium chloride solution, which with advantage can be up to 15%, preferably 8–10%. The plate 6 absorbs immediately the solution. The protection paper is removed and the electrode is applied.

Alternatively it is also possible that the carbon-containing plate 6 can be prepared with a content of dry salt, which is then soaked just before the electrode is to be applied on the skin, and it is also possible that the salt can be moistened by the body liquids or the natural humidity of the body.

Since no metal is used the manufacture will be very simple and cheap and if the electrode is stored dry it can be stored during a long time without being harmed.

On the top side of the elevated center section 2 of the electrode is arranged an electrical contact 3 comprising a neck 7 and on top of this is located the widened top 8. The diameter of the top 8 is 4 mm and the diameter of the neck 7 is a couple of tenths of mm thinner. The contact 3 fits to internationally approved and usually used contacts on patient cables (not shown).

The invention is of course not limited to the embodiments described above but a number of modifications are possible within the scope of the claims. Thereby it is possible to manufacture the electrode with another design or size. The center section 2 of the electrode may for example by designed either with smaller or larger diameter and the effective diameter of the electrode can be chosen in such a way that a better ability and conductivity is achieved. At the so called work-EKG-monitoring the electrode is exposed to larger mechanical strains than is normally the case and it is convenient in these cases to use an electrode which has a larger adhesive surface and/or contact surface. It is thereby possible to design the electrode as an oblong tape or the like the underside of which is provided with a strip of carbon fibre textile. For the connection to the patient cables is used a carrier element according to the invention.

The electrical connection of the electrode may naturally also be designed in other ways. It is for example common that patient cables are provided with pins with a diameter of 4 mm, whereby the electrode is provided with a socket (not shown) molded in one piece with the electrode.

What is claimed is:

1. A nonmetallic disposable inexpensive electrode, mainly intended to be rapidly fixed on the skin of a patient to achieve noise-free signal detection of signals from the body and including an electrically conductive synthetic resin carrier element, one side of which is provided with an electric contact which is in conductive contact with the carrier element and the other side of which is provided with an adhesive layer and forms the front surface of the carrier element intended to adhere in electrical contact to the skin, wherein the adhesive layer of the front surface of the carrier element has at least one opening wherein is applied a carbon-containing element directly contacting the material of the carrier element, said carbon-containing element is a plate of carbon fibers with carbon fiber ends projecting from the surface of said plate as brushes carrying a relatively large number of carbon particles which facilitates the ion migration between the skin and the carrier element whereby the resistance between the skin and the carrier element is substantially reduced by the interposed carbon fiber plate.

2. A disposable electrode as claimed in claim 1 wherein the carbon-containing element is fixed to the carrier element at least partly.

3. A disposable electrode as claimed in claim 1, wherein the carbon-containing element has a size somewhat bigger than the size of said opening in the adhesive layer and is arranged slightly to overlap the inner edge thereof.

4. A disposable electrode as claimed in claim 1, wherein the carrier element and the electric contact are moulded in one piece of a conductive or semi-conductive material.

5. A disposable electrode as claimed in claim 4, wherein the conductive or semi-conductive material of the carrier element consists of a plastic material mixed by carbon.

6. A disposable electrode as claimed in claim 1, wherein the carbon-containing element is supplied with a contact-improving salt solution prior to its application to the area of intended use.

7. A disposable electrode as claimed in claim 1, wherein the carbon-containing element is provided with a content of dry salt intended to be soaked prior to or at the application to the area of intended use.

* * * * *